United States Patent [19]

Dinkler et al.

[11] Patent Number: 5,616,117
[45] Date of Patent: Apr. 1, 1997

[54] SELF LOCKING SURGICAL RETRACTOR

[75] Inventors: Charles Dinkler; John M. Tew, Jr., both of Cincinnati, Ohio

[73] Assignee: Ohio Medical Instrument Company, Inc., Cincinnati, Ohio

[21] Appl. No.: 581,770

[22] Filed: Jan. 2, 1996

Related U.S. Application Data

[63] Continuation of Ser. No. 510,691, Aug. 3, 1995, abandoned.

[51] Int. Cl.[6] .............................. A61B 1/30; A61B 17/02
[52] U.S. Cl. ......................... 600/232; 600/210; 600/215; 600/219; 600/222; 600/231
[58] Field of Search ..................... 600/201, 210, 600/214, 215, 216, 219, 222, 225, 231, 232, 237, 236, 238, 239, 243; 606/151; 269/226

[56] References Cited

U.S. PATENT DOCUMENTS

| | | |
|---|---|---|
| 1,587,897 | 6/1926 | Cameron . |
| 3,227,156 | 1/1966 | Gauthier . |
| 3,643,655 | 2/1972 | Peronti . |
| 4,254,763 | 3/1981 | McCready et al. . |
| 4,627,421 | 12/1986 | Symbas et al. . |
| 4,747,394 | 5/1988 | Watanabe ................................ 600/232 |
| 4,926,849 | 5/1990 | Downey . |
| 4,989,587 | 2/1991 | Farley ................................ 600/232 X |
| 4,991,566 | 2/1991 | Shulman et al. . |
| 5,052,373 | 10/1991 | Michelson ........................... 600/232 X |
| 5,067,477 | 11/1991 | Santangelo . |
| 5,097,820 | 3/1992 | Shulman et al. . |
| 5,167,223 | 12/1992 | Koros et al. . |
| 5,375,481 | 12/1994 | Cabrera et al. . |
| 5,400,774 | 3/1995 | Villalta et al. . |

FOREIGN PATENT DOCUMENTS

| | | |
|---|---|---|
| 625978 | of 1927 | France . |
| 750583 | 6/1956 | United Kingdom . |

OTHER PUBLICATIONS

Retractor illustrated in AESCULAP Product Brochure for "Microsurgical Lumbar Laminectomy".
*Mechanical Engineering Design*, Fifth Edition, by Joseph Edward Shigley and Charles R. Mischke, p. 329, "Figure 8–4, The Joyce Worm–Gear Screw Jack".

*Primary Examiner*—Richard J. Apley
*Assistant Examiner*—Beverly M. Flanagan

[57] ABSTRACT

A medical retractor having a support shaft on which is threaded a retractor arm drive that supports a retractor arm. The retractor arm drive includes a worm with threads that engage peripheral gear teeth of a worm gear; and the worm gear is threaded onto the support shaft. Rotating the worm, turns the worm gear and moves the retractor arm drive and retractor arm longitudinally along the support shaft. A stop prevents the support shaft from rotating with the worm gear in response to rotation of the worm.

17 Claims, 2 Drawing Sheets

SELF LOCKING SURGICAL RETRACTOR

This is a continuation of application Ser. No. 08/510,691 filed on Aug. 3, 1995 now abandoned.

FIELD OF THE INVENTION

This invention relates generally to the field of surgical instruments, and more particularly, to a self locking retractor for spreading apart tissues, membranes and vessels during medical procedures.

BACKGROUND

Surgical retractors for holding tissues at the edge of a surgical incision or wound, away from the field of an operation, have been in use for many years. One style of retractor is shown in the Michelson U.S. Pat. No. 5,052,373. A first retractor arm is attached to one end of a rack and a second retractor arm is moved along the rack by rotating a gear that engages the rack teeth. Typically the second retractor arm is locked into a desired position on the rack teeth by means of a pivotally mounted pawl which is engaged in the rack teeth. The pawl is pivoted to disengage it from the rack teeth, so that rotating the gear will move the second retractor arm to a new position on the rack. With that construction, two manual operations, that is, releasing the pivoting pawl and rotating the gear, are required to change the spacing between the retractor arms. Those manual operations require two hands; and further, if the surgeon has one hand otherwise engaged in the surgical procedure, changing the position of the retractor arm requires two people. Therefore, such a construction has the disadvantage of being relatively difficult to use in the surgical situation.

Another retractor design does not include a locking pin or pawl, but instead, relies on the torquing force on the retractor arm to bind the retractor arm on the rack as the arms are spread apart. While such a design operates satisfactorily, there is always a potential that the spreading force component on the retractor arm that is in the longitudinal direction along the rack might cause the retractor arm to unpredictably slide or slip on the rack. Any unanticipated motion of a retractor arm during a surgical procedure is an obvious disadvantage of the mechanical design.

Other retractor arm designs permit the retractor arm length to be changed by sliding the retractor arm with respect to the supporting cross bar or rack. However, in those designs, it is necessary that the retractor arm be locked or latched into its new position by means of a thumb screw or other mechanism. Again, as with other manual locking devices, the process of changing the length of the retractor arm has the disadvantage of requiring several manual operations.

SUMMARY OF THE INVENTION

The present invention provides a medical retractor having retractor arms that are self locking as their relative spacing and lengths are changed. Further, the relative position and length of the retractor arms may be readily adjusted without manipulating latches, locks or other engagement devices.

In accordance with the principles of the invention, a medical retractor has a support shaft with external threads and a retractor arm drive mounted on the support shaft and supporting a retractor arm. The retractor arm drive includes a worm with threads that engage gear teeth around the periphery of a worm gear. The worm gear is threaded onto the support shaft. Therefore, rotation of the worm rotates the worm gear which moves the retractor arm drive and associated retractor arm longitudinally along the threaded support shaft.

In another aspect of the invention, the medical retractor includes a second retractor arm drive mounted on the support shaft and supporting a second retractor arm. The second retractor arm drive is identical in construction and operation to the first retractor arm drive. In a further aspect of the invention, each of the retractor arm drives has a stop surface or blocking surface for preventing the support shaft from rotating or turning with the respective worm gears.

In a further aspect of the invention, the medical retractor has retractor blades that are retained and guided along the retractor arms by downwardly projecting tongues that are disposed in grooves that extend longitudinally along the upper surface of the retractor arms.

These and other objects and advantages of the present invention will become more readily apparent during the following detailed description together with the drawings herein.

DETAILED DESCRIPTION OF THE INVENTION

Figure 1:
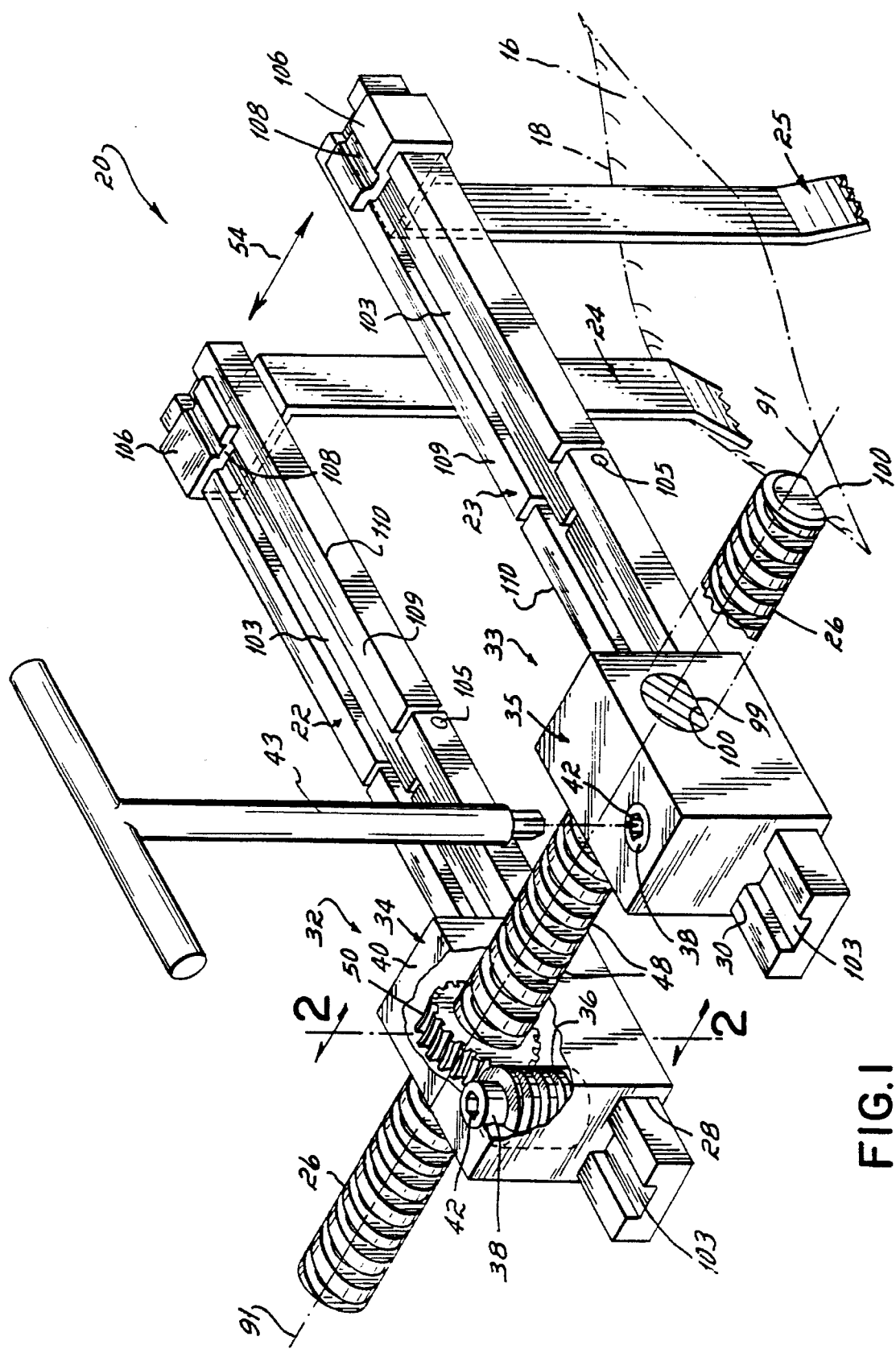
FIG. 1 is a partial cut-away perspective view of the medical retractor in accordance with the principles of the present invention.

Referring to FIG. 1, an incision 16 in body tissue 18, shown in phantom, is spread apart and held spread apart by a medical retractor 20. The retractor 20 includes retractor arms 22, 23 which are carried on a retractor crossbar or support shaft 26. Retractor blades 24, 25 are mounted near the ends of the respective retractor arms 22, 23. The retractor blades 24, 25 extend into the incision 16 and spread the tissue 18 to open the incision 16, thereby facilitating surgical procedures. The retractor blades 24, 25 and their mounting on the retractor arms 22, 23 may be of any known design. The retractor arms 22, 23 preferably have a rectangular cross-section and slide longitudinally freely within openings 28, 30 of the retractor arm drives 32, 33, respectively. The retractor arm drives 32, 33 include drive housings 34, 35, respectively, that contain drive components which may be identical and therefore, only the components within the drive housing 34 will be described in detail. The openings 28, 30 have a cross-section that is sized and shaped to accept the cross-section of the respective retractor arms 22, 23.

A worm 36 is rotatably mounted within the drive housing 34 and has an upper end 38 which extends through the upper surface 40 of the drive housing 34. The upper end 38 of the worm has an opening 42 formed therein that is preferably hexagonal for receiving a wrench having a hexagonal cross-section, for example, an Allen wrench 43 shown in phantom. A driven worm gear 44 is also rotatably journalled in the housing 34 and has internal threads 46 that mate with and receive external threads 48 on the support shaft 26. The illustrated and preferred threads 46, 48 are Acme threads which have a profile with surfaces that extend generally perpendicularly from the centerline of the shaft 26 and therefore, are most effective to resist the forces that act in a generally longitudinally direction along the shaft 26. However, other tread profiles may also be used. The worm gear 44 further has approximately thirty circular pitch, peripheral gear teeth 50 which are sized and shaped to engage with the threads 52 on the worm 36. Rotation of the worm 36 rotates worm gear 44 on shaft 26 which, in turn, causes the drive housing 34, the retractor arm 22 and retractor blade 24 to move in an axial direction 54 along the support shaft 26.

Figure 2:
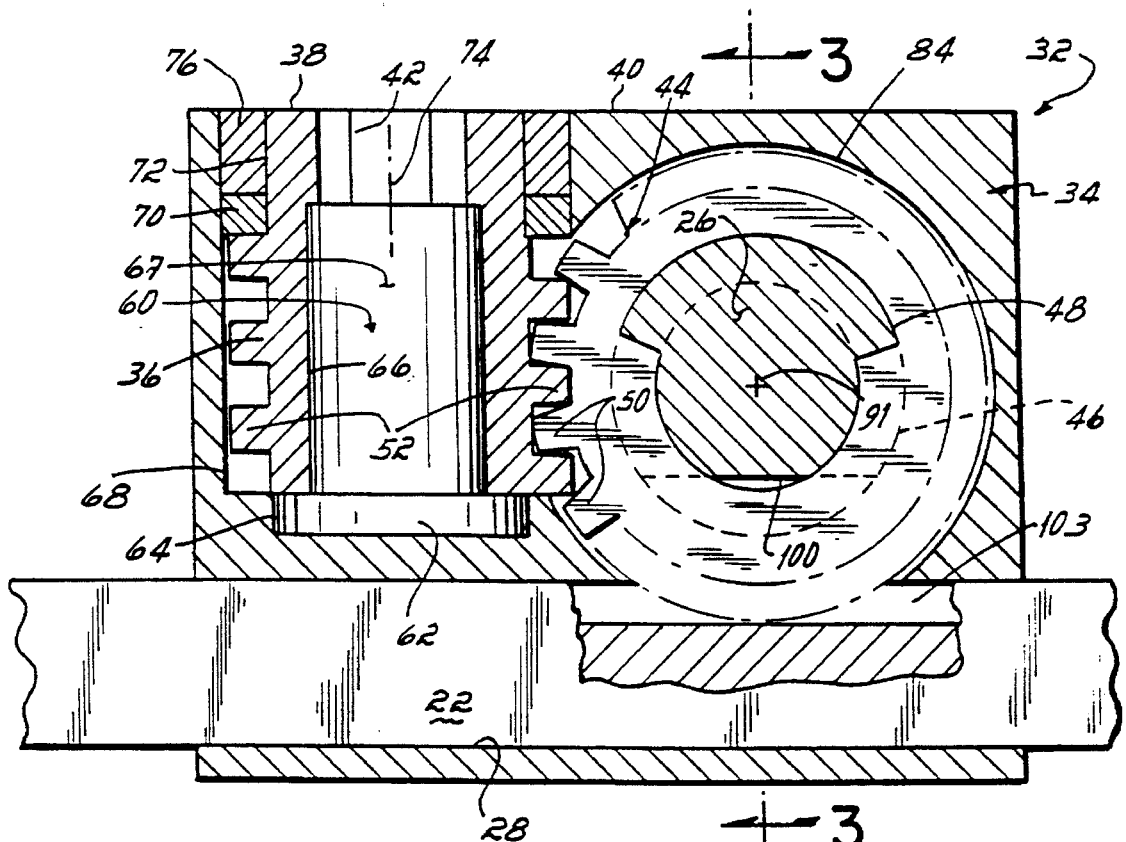
FIG. 2 is a cross-sectional view taken along line 2—2 of FIG. 1.
Figure 3:
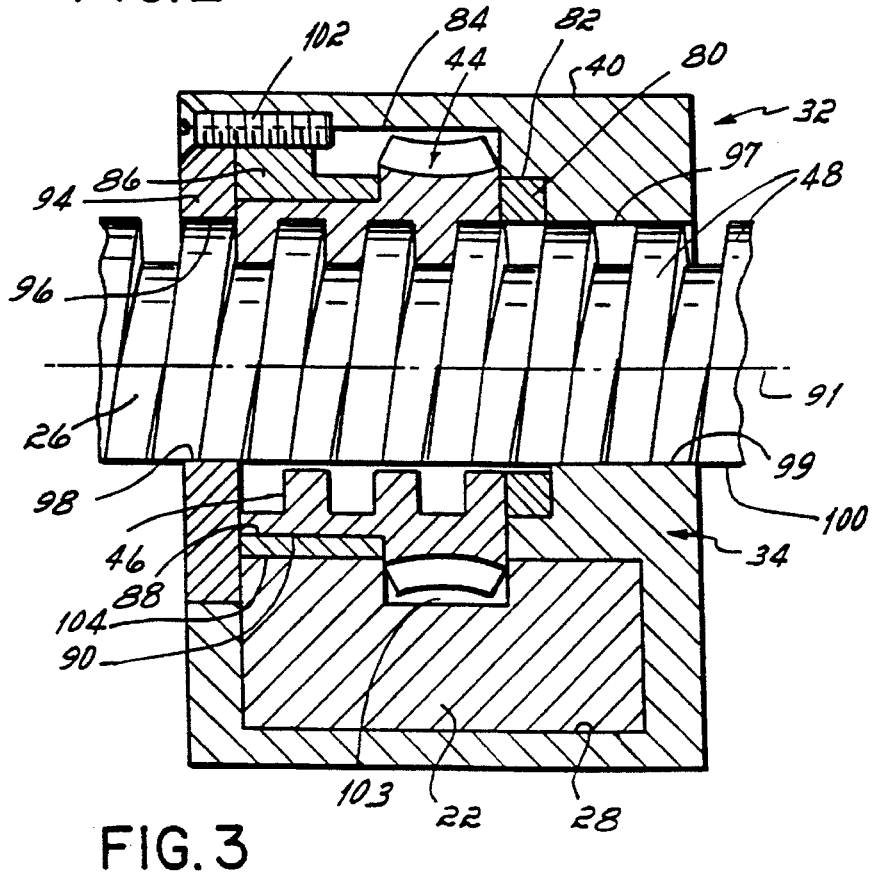
FIG. 3 is a cross-sectional view taken along line 3—3 of FIG. 2.

FIGS. 2 and 3 illustrate the construction of the retractor arm drive 32 in more detail. A cylindrical worm guide bearing 60 has a lower cylindrical flange 62 which is located in a bore 64 within the housing 34. The worm 36 has a four start thread with a 0.26 lead and has an internal bore 66 that slides over a bushing portion 67 of the worm guide 60. The worm 36 also slides and is freely rotatable within an internal bore 68 of the housing 34. A wear washer 70 is adjacent to the upper portion 72 of the worm 36. The wear washer 70 fits snugly within the bore 68 of the housing 32. Consequently, the flange 62 within the bore 64 and the washer 70 between the worm 36 and the internal bore 68 are effective to establish and maintain an axis of rotation 74 for the worm 36. A worm cap or retainer 76 fits over the upper portion 72 of the worm 36 and is press fitted within the opening 68 of the housing 34. The worm cap 76 retains the wear washer 70, worm 36 and worm guide 60 within the bore 68 of the housing 34. Preferably the wear washer 70 is made from a softer material than the worm 36 and the worm cap 76, so that the worm washer is consumed as a wear component instead of the worm 36.

FIG. 3 illustrates the detailed mounting of the worm gear 44 within the housing 34. A wear washer 80 is located in a first bore or seat 82 within the housing 34. The worm gear 44 is rotatably located within a second bore 84 of the housing 34 to have an axis of rotation 91 that is preferably collinear with the center line of the shaft 26 and is generally perpendicular with the axis of rotation 74 of the worm 36. The internal threads 46 of the worm gear 44 mate with the external threads 48 of the retractor support shaft 26. Each of the mating threads 46, 48 is preferably a four start thread with an approximately one-half inch lead. A bushing 86 has an internal bore 88 that fits over a cylindrical portion 90 of the worm gear 44. The bushing 86 has an external diameter that is sized to fit snugly within the internal bore 84 of the housing 34, and therefore, the bushing 86 is effective to hold and stabilize the axis of rotation 91 of the worm gear 44. As illustrated in FIGS. 2 and 3, the worm 36 and its associated components rotate about an axis of rotation 74 that is offset from and transverse to the axis of rotation 91 about which the worm gear 44 and its associated components rotate.

A worm gear cap 94 and housing 34 have openings 96, 97 that are generally cylindrical but have flats, or chords 98, 99, respectively, extending across and truncating the circular profile of the bores 96, 97. Referring to FIG. 2, the cross-section of the support shaft 26 is generally cylindrical but has a flat, or chord, 100 extending across and truncating the circular profile. The bores 96, 97 and their associated flats 98, 99 define a profile which is sized and shaped to accept and slide over the cross-section of the retractor support shaft 26 with its flat 100. The flat surfaces 98, 99 and adjacent flat surface 100 on shaft 26 block rotation of the shaft 26 with respect to the housing 34, that is, the shaft can be moved axially relative to the housing, but cannot rotate in it. In the absence of the adjacent flats or stop, the retractor support shaft 26 might follow the rotation of the worm gear 50. Rotating the worm 36 could otherwise result in worm gear 50 and support shaft 26 rotating together; and in that situation, worm gear 50 would not move longitudinally along the support shaft 26. Referring back to FIG. 3, the worm gear cap 94 is press fit into the bore 84 of the housing 34 so that worm gear cap cannot rotate with respect to the housing 34. Further, the flats 98, 99 on the respective worm gear cap 94 and housing 34 mate with the flat 100 on retractor support shaft 26 to prevent the retractor support shaft 26 from rotating with the worm gear 50. In addition, screws 102 or other fasteners are used to further secure the worm gear cap 94 from rotation within the bore 84. The screws 102 are positioned around the periphery of the worm gear cap 94 to secure the cap 94 but not interfere with the operation of the retractor arm drives 32, 33.

Referring to FIG. 1, in use, one or more wrenches 43 are inserted in one or both of the sockets 42 in the opposite ends of worms 36. The wrenches are used to rotate the worms thereby moving the retractor arm drives 32, 33 axially along the shaft 26 until they are located in desired relative positions. Preferably, rotating the worms clockwise moves the retractor arms 22, 23 to the right, and rotating the worms 36 counter-clockwise moves the retraction arms 22, 23 to the left as viewed in FIG. 1. on. One revolution of the worm moves the respective retractor arms approximately one-tenth of an inch. Often, the retractor arms 22, 23 are initially located substantially adjacent to each other. In that position, the effective length of the retractor arms 22, 23 can be easily adjusted by sliding the retractor arms 22, 23 within the openings 28, 30 of the drives 32, 33 in a direction generally perpendicular to the shaft 26. Therefore, the length of the retractor arms 22, 23 can be adjusted without requiring manipulation of a latch, lock or other mechanism.

In adjusting the retractor arms 22, 23 to their desired length, it may be desirable to bend or pivot the retractor arms 22, 23 with respect to their pivot pins 105. Therefore, the mass of the retractor may be rested on a surface that is not aligned with the surface of the incision 16. The retractor blades 24, 25 are then slid into the incision 16 in the tissue 18 that is to be separated by the retractor 20. Each of the retractor blades 24, 25 has a connector 106 at its upper end that is sized and shaped to slide over a respective retractor arm 22, 23. Further, each connector 106 has a downward extending tongue or projection 108 that is inserted into the longitudinal grooves or slot 103 of the respective retractor arms 22, 23. Preferably, the grooves 103 are centered longitudinally along the upper surface 109; however, the grooves 103 could be located along an edge of the retractor arms, for example, the edges 110, so that the grooves are still effective to prevent the retractor blades from sliding laterally or sideways off of the retractor arms 22, 23. The disposition or location of the projections 108 in the grooves 103 helps retain the retractor blades 24, 25 on the retractor arms 22, 23 and further, provides a guide in moving the retractor blades 24, 25 to different positions along the length of the respective retractor arms 22, 23. To reduce weight and facilitate use, the assembly of parts within the retractor drives 32, 33 are made as compact as possible. Therefore, each of the retractor arms 22, 23 contains a clearance slot or groove 103 which receives the peripheral gear teeth 50 of the respective rotating worm gear 44. In addition, referring to FIG. 3, the cylindrical bushing 86 in each of the retractor arm drives 32, 33 has a flat 104 on one side to provide clearance for the sliding retractor arms 22, 23.

The worms 36 within one or both of the retractor arm drives 32, 33, are then rotated to move the retractor arm drives 32, 33, retractor arms 22, 23 and associated retractor blades 24, 25 away from each other thereby spreading the tissue apart. Again, the length of the retractor arms 22, 23 can be easily slidably adjusted. As the tissues are spread apart, the reactive forces on the retractor blades 24, 25 tending to push the retractor arms 22, 23 together, will increase substantially. Those forces are generated in a direction generally axially or longitudinally with respect to the shaft 26. Since the retractor gear 44 is threaded onto the shaft 26, that threaded engagement prevents the worm gears 44 within the associated retractor arm drives 32, 33 from being moved axially along the shaft 26 by the retraction forces. Therefore, the worm and worm gear drive within the retractor arm drives 32, 33 are self-locking and provide a very stable positioning of the retractor arms 22, 23. Further, the mechanical advantage provided by the worms 36 and worm gears 44 within the retractor arm drives 32, 33 allow the retractor arms to be easily moved with little effort along the shaft 26 even though there are substantial reactive forces being applied to the retractor arm blades 24, 25. While those substantial reactive forces do not hinder or impede motion of the retractor arm drives 32, 33 along the shaft 26, they are effective to provide a torsional or "cocking" force component on the retractor arms 22, 23 with respect to the openings 28, 30. That torsional force component effectively binds or locks the retractor arms 22, 23 at their desired length with respect to the retractor arm drives 32, 33.

While the invention has been set forth by a description of the preferred embodiment in considerable detail, it is not intended to restrict or in any way limit the claims to such detail. Additional advantages and modifications will readily appear to those who are skilled in the art. For example, if the drive housings 34 are made larger, the retractor arms 22, 23 can be moved downward from the support screw 26 as viewed in FIGS. 2–3. That would eliminate the interference between the worm gears 44, retractor arms 22, 23 and the bushing 86; and therefore, flat 104 on the bushing 86 could be eliminated. In that situation, if the tongues 108 on the retractor blade connectors 106 are not used, the grooves 103 could be eliminated.

Further, it is preferable that the support shaft 26 be positively prevented from rotating with the worm gear 44 in response to rotation of the worm 36. However, the stop surfaces, that is, flat surfaces 98, 99 and 100 could be eliminated, and the shaft 26 can be restrained from motion with the worm gear by other means. For example, the shaft 26 can be manually held in place, or if there is a low resistance interface between the details shown and described. Consequently, departures may be made from the details described herein within departing from the spirit and scope of the claims which follow.

What is claimed is:

1. A medical retractor for holding open an incision in a body tissue comprising:
   a support shaft having threads on an outer surface thereof;
   a first retractor arm;
   a first retractor arm drive supporting and moving the first retractor arm and including
   a first worm gear rotatably mounted within the first retractor arm drive and having
   a bore with internal threads sized and shaped to receive and rotate on the threads on the support shaft, and
   worm gear teeth around the first worm gear;
   a first worm having threads and rotatably mounted within the first retractor arm drive with the threads on the first worm engaging the worm gear teeth, and
   a second retractor arm mounted on the support shaft, whereby rotating the worm turns the worm gear, thereby moving the first retractor drive and the first retractor arm in an axial direction along the support shaft with respect to the second retractor arm.

2. The medical retractor of claim 1 wherein the first retractor arm drive further includes a stop which prevents the support shaft from rotating when the first worm gear is rotated to move the first retractor arm drive and the first retractor arm axially along the shaft.

3. The medical retractor of claim 2 wherein the first retractor arm drive further includes a first housing having an opening sized and shaped to receive the first retractor arm.

4. The medical retractor of claim 3 wherein the stop further comprises adjacent surfaces on each of the support shaft and the first housing for preventing relative rotation between the support shaft and the first housing.

5. The medical device of claim 4 wherein the adjacent surfaces are generally flat surfaces.

6. The medical retractor of claim 3 further comprising a second retractor arm drive including
   a second housing having an opening sized and shaped to receive the second retractor arm;
   a second worm gear rotatably mounted within the second housing and having
   a bore with internal threads sized and shaped to receive and engage the threads on the support shaft, and
   worm gear teeth extending around the worm gear;
   a second worm having threads and rotatably mounted in the second housing so that the threads on the second worm engage the worm gear teeth on the second worm gear; and
   a second stop to prevent the support shaft from rotating with the second worm gear.

7. The medical retractor of claim 6 wherein the openings in the first and second housings are approximately perpendicular to the bores in the respective first and second worm gears.

8. The medical retractor of claim 7 wherein the first and the second retractor arms slide axially within the openings of the respective first and second housings.

9. The medical retractor of claim 8 wherein the first and the second retractor arms are locked in a desired longitudinal position within the openings in the respective first and second housings by forces applied to the retractor arms in holding open the incision in the body.

10. The medical retractor of claim 9 wherein the first and second retractor arms have a generally rectangular cross-section and the openings in the respective first and second housings have a mating generally rectangular cross-section.

11. The medical retractor of claim 10 further comprising retractor blades mounted on one end of each of the first and the second retractor arms.

12. The medical retractor of claim 11 wherein the bores of the first and second worm gears are coaxially located with respect to an axis of rotation of the respective worm gears.

13. The medical retractor of claim 12 wherein the worm gear teeth on the first and second worm gears are on a peripheral edge of the respective worm gears.

14. The medical retractor of claim 13 wherein the worm gear teeth on the first and second worm gears extend in a direction generally parallel to the axis of rotation of the respective worm gears.

15. A medical retractor for holding open an incision in a body tissue comprising:
   a support shaft having threads on an outer surface thereof;
   a first retractor arm;
   a first retractor arm drive including a first housing having an opening sized and shaped to receive the first retractor arm, a first worm gear rotatably mounted within the first housing and having
- a bore having internal threads sized and shaped to receive and engage the threads on the support shaft, and
- worm gear teeth around the first worm gear;

a first worm having threads and rotatably mounted in the first housing so that the threads on the first worm engage with the worm gear teeth on the first worm gear;

a second retractor arm;

a second retractor arm drive including
- a second housing having an opening sized and shaped to receive the second retractor arm, and
- a second worm gear rotatably mounted within the first housing and having
  - a bore having internal threads sized and shaped to receive and engage the threads on the support shaft, and
  - worm gear teeth around the worm gear;

a second worm having threads and rotatably mounted in the first housing so that the threads on the worm engage with the worm gear teeth on the worm gear, whereby rotating the first and second worms turns the respective first and second worm gears, thereby moving the respective first and second retractor drives and associated first and second retractor arms in an axial direction along the support shaft.

16. The medical retractor of claim 15 further comprising:

a first stop to prevent the support shaft from rotating with the first worm gear; and a second stop to prevent the support shaft from rotating with the second worm gear.

17. A medical retractor for holding open an incision in body tissue comprising:

a support shaft;

first and second retractor arm drives mounted on the support shaft for longitudinal motion along the support shaft;

first and second retractor arms mounted in the first and second retractor arm drives, respectively, to be generally parallel with each other and extend generally perpendicularly with respect to the support shaft, each of the retractor arms having a groove extending longitudinally and centrally on an upper surface of the respective retractor arm;

first and second retractor blades, each of the retractor blades having a connector at an upper end slidingly mounted on a respective one of the retractor arms, each connector having a projection extending downward into a respective groove of one of the retractor arms, whereby the disposition of the projection into the grooves helps to retain the retractor blades on the respective retractor arms and further helps to guide motion of the retractor blades along the respective retractor arms.

\* \* \* \* \*